(12) United States Patent
Baylor

(10) Patent No.: US 6,475,145 B1
(45) Date of Patent: Nov. 5, 2002

(54) METHOD AND APPARATUS FOR DETECTION OF ACID REFLUX

(75) Inventor: Richard A. Baylor, Champaign, IL (US)

(73) Assignee: Baymar, Inc., Champaign, IL (US)

( * ) Notice: Subject to any disclaimer, the term of this patent is extended or adjusted under 35 U.S.C. 154(b) by 0 days.

(21) Appl. No.: 09/573,136

(22) Filed: May 17, 2000

(51) Int. Cl.⁷ .................................................. A61B 5/00
(52) U.S. Cl. ...................................... 600/309; 600/364
(58) Field of Search ................................ 600/309, 364, 600/348, 350, 361

(56) References Cited

U.S. PATENT DOCUMENTS

| | | |
|---|---|---|
| 3,373,735 A | 10/1965 | Gallagher |
| 3,528,429 A | 9/1970 | Beal |
| 3,608,061 A | 9/1971 | McNally ........................ 424/4 |
| 4,632,119 A | 12/1986 | Reichstein |
| 4,735,214 A | 4/1988 | Berman |
| 5,368,027 A | 11/1994 | Lübbers et al. |
| 5,738,110 A | 4/1998 | Beal et al. |
| 6,006,121 A | * 12/1999 | Vantrappen et al. ........ 600/350 |

OTHER PUBLICATIONS

John Robert Claussen, PA–C, MPAS, *Gastroesophageal Reflux Disease*, Clinician Reviews 9(6):69–72, 75–77, 80–82, 85, 1999, Clinicians Publishing Group and Williams & Wilkins, 1999, pp. 1–8.

H. G. Dammann, MD, *The Relevance of Acidity Measurements in the Management of Gastrooesophageal Reflux Disease*, Research & Clinical Forums 20(2):19–26, 1998 Wells Medical Holdings, Ltd., 1998, pp. 1–7.

R. H. Colson et al., *An Accurate, Long–Term, pH–Sensitive Radio Pill for Ingestion and Implantation*, Biotelemetry Patient Monitg 8: 213–227 (1981).

Gary C. Vitale et al., *Computerized 24–hour Esophageal pH Monitoring: A New Ambulatory Technique Using Radiotelemetry*, J. Lab. Clin. Med., vol. 105, No. 6, Jun. 1985, pp. 686–693.

* cited by examiner

Primary Examiner—Eric F. Winakur
(74) Attorney, Agent, or Firm—Brinks Hofer Gilson & Lione

(57) ABSTRACT

Methods and apparatus for monitoring gastrointestinal pH levels are disclosed. A gastroesophageal diagnostic device for determining the duration of exposure of a patient's esophagus to pH levels clinically significant for gastroesophageal reflux disease is disclosed.

18 Claims, 1 Drawing Sheet

METHOD AND APPARATUS FOR DETECTION OF ACID REFLUX

BACKGROUND OF THE INVENTION

Gastroesophageal reflux occurs when stomach acid intermittently surges into the esophagus. It is common for most people to experience this acid reflux occasionally as heart burn. Gastroesophageal reflux disease (GERD) is a clinical condition in which the reflux of stomach acid into the esophagus is frequent enough and severe enough to impact a patient's normal functioning or to cause damage to the esophagus. GERD is sometimes also referred to as "reflux" or "reflux esophagitis."

It has been estimated by the U.S. Department of Health and Human Services that about seven million people in the United States suffer from GERD. The incidence of GERD increases after the age of 40, and more than 50 percent of those afflicted with GERD are between the ages of 45–64. (Statistics from *Digestive Diseases in the United States: Epidemiology and Impact,* National Digestive Diseases Data Working Group, James E. Everhart, MD, MPH, Editor, U.S. Department of Health and Human Services, Public Health Service, National Institutes of Health, NIH Publication No. 94-1447, May 1994.) For general information about GERD see the following: Fennerty, M. B., Sampliner, R. E., Gastroesophageal reflux disease, *Hospital Medicine,* 29(4): 28–40 (1993); and Orlando, R. C., Reflux esophagitis, in *Textbook of Gastroenterology,* 1: 1123–1147, Yamada, T., ed., J. B. Lippincott Co., Philadelphia, Pa. (1991).

In the lower part of esophagus, where the esophagus meets the stomach, there is a muscular valve called the lower esophageal sphincter (LES). Normally, the LES relaxes to allow food to enter into the stomach from the esophagus. The LES then contracts to prevent stomach acids from entering the esophagus. In GERD, the LES relaxes too frequently or at inappropriate times allowing stomach acids to reflux into the esophagus.

The most common symptom of GERD is heartburn. Acid reflux also leads to esophageal inflammation, which causes symptoms such as odynophagia, or painful swallowing, and dysphagia, or difficulty swallowing. Pulmonary symptoms such as coughing, wheezing, asthma, or inflammation of the vocal cords or throat may occur in some patients. More serious complications from GERD include esophageal ulcers and esophageal stricture, or narrowing of the esophagus. The most serious complication from chronic GERD is a condition called Barrett's esophagus in which the epithelium of the esophagus is replaced with abnormal tissue. Barrett's esophagus is a risk factor for the development of cancer of the esophagus.

Accurate diagnosis of GERD is difficult but important. Accurate diagnosis allows identification of individuals at high risk for developing the complications associated with GERD. It is also important to be able to differentiate between gastroesophageal reflux, other gastrointestinal conditions, and various cardiac conditions. For example, the similarity between the symptoms of a heart attack and heart burn often lead to confusion about the cause of the symptoms.

Several methods are currently being used to diagnose GERD and its associated complications. In healthy subjects, esophageal pH values are greater than pH 4 most of the time, and are lower than pH 4 only a very small percentage of the time. Therefore, an esophageal pH of less than pH 4 is generally used as the threshold to determine the presence of excessive acid reflux. See, e.g. H. G. Dammann, M.D., University of Hamburg, Hamburg Science Institute for Clinical Research "The Relevance of Acidity Measurements in the Management of Gastro-oesophageal Reflux Disease," *Research & Clinical Forums,* 20(2):19–26 (1998) (healthy subjects had an esophageal pH of less than pH 4 approximately 1.5% of the time within a twenty-four hour period); and Jamieson J. R., Stein H. J., DeMeester T. R., Bonavina L., Schwizer W., Hinder R. A., and Albertucci M., "Ambulatory 24-hour esophageal pH monitoring: normal values, optimal thresholds, specificity, sensitivity, and reproducibility," *Am. J. Gastroenterol.,* 87(9):1102–11 (1992).

It is difficult to accurately test esophageal pH because the episodes of acid reflux into the esophagus are sporadic even in patients with severe reflux disease. Within a twenty-four hour period, the episodes of reflux may only occur about 10 to 15 percent of the time. See, e.g. Fink, S. M., and McCallum, R. W., "The role of prolonged esophageal pH monitoring in the diagnosis of gastroesophageal reflux," *JAMA,* 252(9):1160–64 (1984) (during 24-hour pH monitoring, the mean percentage time that pH was less than pH 4.0 was approximately 13.2% for GERD patients, and approximately 2.9% for normal subjects); and Vitale, G. C. et al., "Computerized 24-hour ambulatory esophageal pH monitoring and esophagogastroduodenoscopy in the reflux patient: a comparative study," *Ann. Surg.,* 200(6):724–728 (1984) (the mean length of time of reflux below pH 4 was 5.41 minutes/hour, or approximately 9 percent of the time, in patients with reflux symptoms, and 0.70 minutes/hour, or approximately 1.2 percent of the time, in normal subjects). At any given time, the esophageal pH is likely to be normal. Therefore, it is important to assess the total time during which the esophagus is exposed to a clinically significant low pH over an extended period of time, such as twenty-four hours.

These studies indicate that in patients who exhibit symptoms of reflux, the percentage of time during which the esophageal pH is less than pH 4 may vary, and may be in the range of only ten to fifteen percent of the time. In normal subjects, esophageal pH is less than pH 4 only a very small percentage of the time, typically between one to three percent of the time. Therefore, an esophageal pH of less than about pH 4 for about five or more percent of the time is indicative of the symptoms of reflux. The percentage of time during which the patient's esophagus is exposed to pH levels less than about pH 4 is correlated with the severity of the disease—the greater the time of exposure, the more severe the condition. An esophageal pH of less than about pH 4 for about ten or fifteen percent of the time is indicative of more severe GERD.

Esophageal manometry, esophageal endoscopy, and esophageal pH monitoring are standard methods of measuring esophageal exposure to stomach acids and are currently used to diagnose GERD. Conventional pH monitoring involves placing a pH probe in the esophagus. Preferably, esophageal pH monitoring would take place over a twenty-four hour period.

Several methods of gastrointestinal pH monitoring have been used including intubation methods, ingestible capsules, glass electrodes, and radiotelemetry pills. Intubation involves the insertion of a tube into the patient. The tube is inserted through the nose and into the gastrointestinal tract of the patient. There may be a device at the inserted end of the tube which allows retrieval of a sample for further analysis, as disclosed in U.S. Pat. No. 4,735,214. Alternatively, the tube may be associated with an acid-base indicator, as disclosed in U.S. Pat. No. 3,373,735. Intubation methods are generally used for pH monitoring at a specific time, which does not allow for a determination of time exposure to clinically significant low pH. Intubation is also painful and uncomfortable, and it must be carried out in a hospital or clinical setting.

Tubeless methods and ingestible capsules have also been used to measure gastrointestinal pH. Ingestible capsules have been used to determine pH levels at a specific time and to retrieve samples from the gastrointestinal tract of a patient for further analysis. An ingestible capsule using an ion-exchange color indicator has also been suggested for use in twenty-four hour monitoring of esophageal pH, as disclosed in U.S. Pat. No. 4,632,119.

Electronic pH monitoring devices have also been used. A glass electrode or a radiotelemetry pill is introduced nasally or orally and is positioned in the esophagus proximal to the LES. The pH probe is connected to a microprocessing unit and pH levels are continuously recorded over a twenty-four hour period. (See, Colson, et al., "An Accurate, Long-Term, pH-Sensitive Radio Pill for Ingestion and Implantation," *Biotelemetry Patient Monitg.*, 8: 213–227 (1981). This type of monitoring may take place in a hospital or clinic. Alternatively, with a portable microprocessor, the patient may be ambulatory. Even with a portable unit, the procedure is uncomfortable, and the apparatus is cumbersome. The probe is passed through the nose, and wires extending from the probe course over the face, across the chest, and attach to a recording device worn on a belt. Both the appearance of the apparatus and the discomfort it causes may restrict a patient from engaging in his normal daily activities, thus interfering with the diagnostic result. Additionally, electronic pH monitoring is expensive and requires computer analysis of the data gathered.

BRIEF SUMMARY OF THE INVENTION

In one aspect, the present invention provides methods and apparatus for a gastrointestinal pH monitor utilizing an ingestible and retrievable radioactive capsule swallowed and held in the esophagus by means of a cord. Presence of acid in the esophagus causes pH-dependent degradation of the capsule and a decrease in the amount of radioactivity in the capsule. The capsule is assayed before and after placement in the esophagus and the residual radioactivity is correlated with overall acid exposure over a given period of time.

In another aspect, the present invention provides methods and apparatus for an ambulatory gastrointestinal diagnostic device which provides a semiquantitative determination of the duration of esophageal exposure to pH levels clinically significant for gastroesophageal reflux disease.

In another aspect, the present invention provides methods and apparatus for a gastrointestinal diagnostic device that is inexpensive, comfortable, and easy to use and does not interfere with a patients normal daily activities, allowing accurate twenty-four hour analysis of the patient's gastrointestinal tract.

In another aspect, the present invention provides methods and apparatus for diagnosing gastroesophageal reflux disease.

DETAILED DESCRIPTION OF THE PRESENTLY PREFERRED EMBODIMENTS

Figure 1:
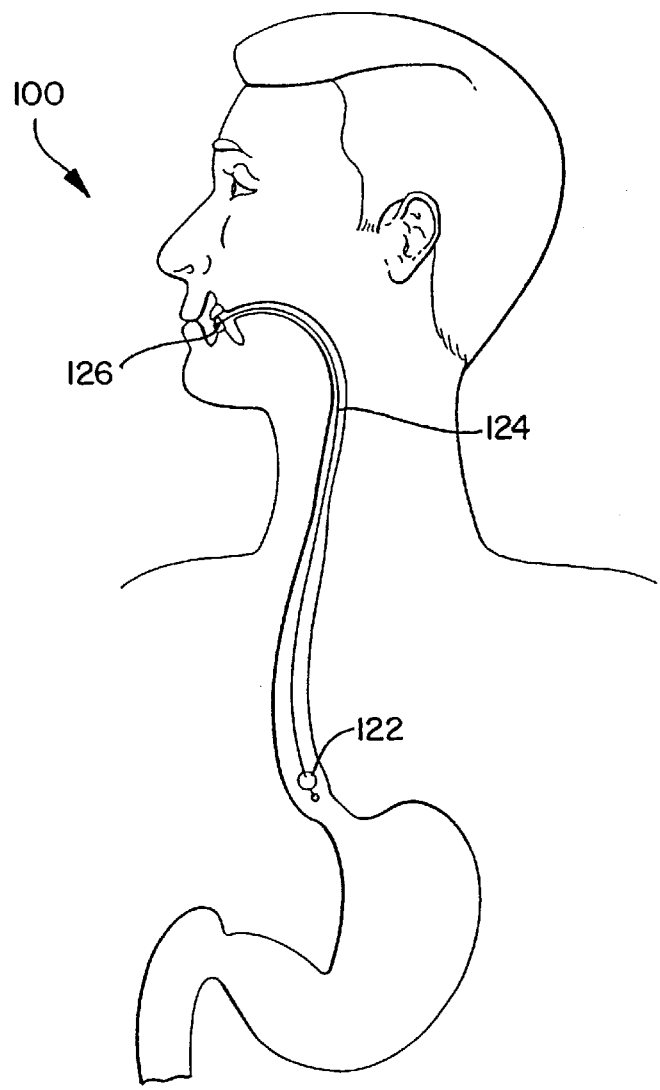
FIG. 1 is a schematic illustration of the gastrointestinal diagnostic capsule of the present invention illustrating the manner in which it is inserted into a patient.

The present invention is directed to methods and apparatus for monitoring pH levels in the gastrointestinal tract of a patient. The present invention is more particularly directed to methods and apparatus for determining the duration of exposure of the esophagus to pH levels clinically significant for gastroesophageal reflux disease.

The phrases "low pH," "pH levels clinically significant for gastroesophageal reflux disease," and the like refer to pH levels less than about pH 4.

The terms "gastroesophageal device" or "gastroesophageal diagnostic device" and "gastrointestinal device" or "gastrointestinal diagnostic device" are all used to generally describe a device according to the present invention. The term "gastroesophageal" is used to specifically refer to the use of a device according to the present invention to monitor pH in the esophagus. The term "gastrointestinal" is used more generally to reflect that the scope of the present invention includes the use of a device according to the present invention to monitor pH in other areas of the gastrointestinal tract.

According to a preferred embodiment of the present invention, a system is described below that provides for a device comprising an ingestible but retrievable capsule for monitoring esophageal pH. The capsule has a cord connected to it and contains a radioactive material distributed throughout. The cord has two ends, a proximal end and a distal end. For clarity, the end of the cord nearest to the capsule is referred to as the proximal end of the cord because when the capsule is inserted into the patient, this end is inserted first and is proximal to the LES. The distal end of the cord is the opposite end of the cord which remains accessible to the patient and/or the clinician. The amount of radioactivity in the capsule is quantified before ingestion of the capsule by the patient. The patient retains the loose, or distal, end of the cord and swallows the capsule. The capsule is suspended in the lower esophagus and held in place with a cord. The capsule is preferably positioned in the lower one-third of the esophagus. The position of the capsule can be monitored by detection of the radioactivity in the capsule, by x-ray, or by measurement of the cord itself, and can be controlled with the cord. Once properly positioned, the distal end of the cord may then be anchored in the patient's mouth or taped to the patient's face. The patient then proceeds with his normal daily activities. The radioactive material from the capsule is released over time as the capsule is exposed to pH levels clinically significant for acid reflux. After approximately twenty-four hours, the capsule is removed from the patient and the level of radioactivity is once again quantified. The decrease in the level of radioactivity in the capsule is correlated with the duration of time that the patient's esophagus is exposed to low pH. The longer the exposure to acidic conditions, the greater the decrease in radioactivity in the capsule. This information is used to diagnose gastroesophageal reflux.

One preferred embodiment of a gastrointestinal diagnostic device 100 is shown in FIG. 1 which illustrates the use of the device 100 in a patient. The capsule 122 is suspended in the lower esophagus. A cord 124 is attached to the capsule. The cord 124 is used to suspend the capsule at the appropriate position in the esophagus of the patient and to retrieve the capsule. At the distal end of the cord, is an attachment member 126. The attachment member 126 is used to attach the cord to a location on the patient while the device is in use.

Figure 2:
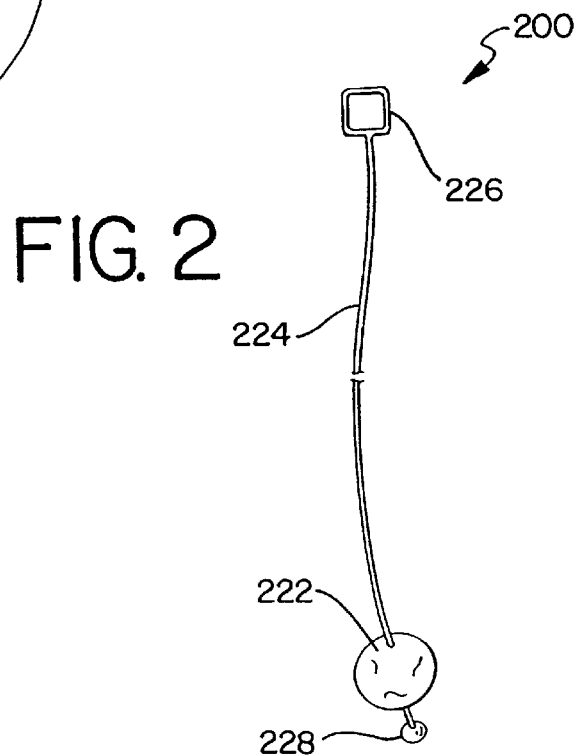
FIG. 2 is a schematic illustration of the gastrointestinal diagnostic capsule of the present invention.

Another embodiment of a gastroesophageal diagnostic device according to the present invention is shown in FIG. 2. The capsule 222 is sized and shaped to be readily swallowable. The capsule 222 is of a size that is easily ingestible and does not interfere with digestion or swallowing when positioned a patient's esophagus. The capsule 222 is preferably made of a polymer, resin, or other non-toxic material which is biocompatible and inert. The capsule is preferably resistant to degradation at pH 4 and above, and subject to degradation when exposed to pH levels lower than pH 4. The rate of degradation of the capsule at pH levels lower than pH 4 is preferably slow enough so a detectable amount of radioactivity remains in the capsule after exposure to clinically significant pH levels in the esophagus of a patient over a twenty-four hour period.

Many polymers have been developed for controlled-release delivery systems. Such systems rely on the chemical nature of a specific type of polymer to regulate the rate of polymer degradation under various conditions. Polymers commonly used to control release in a pH-dependent manner include derivatives of polyacrylates, derivatives of polymethacrylates, polyvinyl derivatives, and cellulose derivatives. For example, EUDRAGIT® polymers, manufactured by Röhm America, Inc., have been developed to be soluble in gastric juices but not at neutral pH levels. Hydrogels, or polymers that swell without dissolving, have also been developed for use in pH-dependent delivery. For additional information on pH-dependent biodegradable polymers, see *Biomedical Polymers: Designed-to-Degrade Systems,* S. W. Shalaby, Ed., Hanser, N.Y., 1994.

In one embodiment, a surface-eroding polymer is used. A surface-eroding polymer is a biodegradable polymer that degrades only at the exposed surface, so the release rate of radioactive isotope is proportional to the surface area of the capsule. Examples of polymers that show surface erosion, as opposed to a bulk-erosion, include polyanhydrides and polyorthoesters.

One alternative to controlling the rate of polymer degradation is to encapsulate the radioisotope and control its release by controlling polymer permeability. The capsule can be surrounded by a pH-sensitive semipermeable membrane. The membrane would allow release of the content of the capsule only under conditions of pH levels less than about pH 4.

In one embodiment, the capsule preferably is made with a radioisotope uniformly dispersed throughout. The amount of radioactivity in the capsule is sufficient to yield a detectable level of radioactivity after exposure to the esophagus of a patient for about twenty-four hours. After exposure, the level of radioactivity in the capsule is reduced by radioactive decay, which is dependent on the half-life of the isotope, and by degradation of the capsule, which is dependent on the amount of time the capsule is exposed to a clinically significant low pH.

In one embodiment, the radioisotope is preferably a gamma emitter with a half-life of about two to three days, and is used at a level of about three to four micro-Curies ($\mu$Cu) in the capsule. The amount and type of isotope is chosen to yield sufficient counts for detection, and to maintain a safe level of exposure for the patient.

In an alternate embodiment, the amount of radioactivity in the capsule is less than about three micro-Curies ($\mu$Cu). In another embodiment, the amount of radioactivity in the capsule is greater than about four micro-Curies ($\mu$Cu).

Non-exhaustive examples of radioactive isotopes which may be used in the present embodiment are shown in Table 1.

TABLE 1

| Radioisotope | Symbol | Half-life |
| --- | --- | --- |
| Molybdenum-99 | Mo-99 | 2.7 days |
| Indium-111 | In-111 | 2.8 days |
| Thallium-201 | Tl-201 | 3 days |
| Gallium-67 | Ga-67 | 3.26 days |
| Iodine-131 | I-131 | 8 days |

Alternatively, radioisotopes with longer or shorter half-lives can be used. Other radioisotopes, with longer half-lives, commonly used in therapeutic and diagnostic applications include Palladium-103 (half-life 17 days) and Iodine-125 (half-life 59.4 days). Radioisotopes with shorter half-lives include Iodine-123 (half-life 13 hours) and Xenon-133 (half-life 5.3 hours). Any isotope which yields sufficient radioactivity for detection, and maintains a safe level of exposure for the patient can be used.

In a preferred embodiment, the capsule is left in the esophagus of a patient for approximately twenty-four hours. A twenty-four hour period of time is preferred because it allows exposure of the capsule to the esophagus of a patient for a complete daily cycle. It is also possible, however, to leave the capsule positioned in a patient's esophagus for periods of time greater than twenty-four hours or less than twenty-four hours. In one alternate embodiment, the capsule is retained in the patient's esophagus for approximately twelve hours.

A cord 224 is attached to or embedded in the radioactive capsule. The cord 224 is long enough to extend distally outside the patient while the capsule is located at the desired position in the esophagus. The cord 224 may optionally include measuring indicia. The cord 224 can be calibrated with a non-toxic dye to aid in the determination of the location of the capsule. Like the material of the capsule 222, the cord 224 is preferably made of a material that is non-toxic and inert. The cord can be made of any thin, flexible material. Examples of materials that may be used for the cord 224 include string, nylon cord, fishing line, or various types of surgical sutures.

An attachment member 226 is positioned at the distal end of the cord. The attachment member 226 allows anchoring of the distal end of the cord 224 and helps maintain the capsule 222 in its desired position in the patient. The attachment member 226 may be detachable from the cord or adjustable on the cord to allow the attachment member 226 to be easily positioned at the desired location. The attachment member 226 is preferably a material that is non-toxic and inert. The exact shape of the attachment member 226 depends on the specific attachment site. The attachment site is preferably at a location that is relatively easy for the clinician to access and that does not significantly interfere with the normal functioning or the daily routine of the patient.

In one embodiment, as seen in FIG. 1, the attachment site is at one or more of the patient's teeth. In this case, the attachment member 126 (226 in FIG. 2) may be a cap that fits over one or more of the patient's teeth. The cap can be removably affixed or cemented to one or more of the patient's teeth to increase its stability.

Alternatively, the attachment member 226 may simply be part of the cord 224 itself, particularly if the attachment site is one or more of the patient's teeth. For example, the attachment member 226 may be a loop in the cord, positioned at the distal end of the cord, which wraps around one or more of the patient's teeth and holds the device 200 in place. Alternatively, the cord can be taped to the patient's face or to some other area.

There may optionally be a weight 228 positioned adjacent to the capsule 222 which helps guide the capsule 222 down the gastrointestinal tract when the capsule 222 is ingested. The weight 228 also helps maintain the capsule 222 in its desired position while in place in the patient. The weight 228 is preferably made of an inert, nontoxic, material with a density greater than that of the capsule. The weight is preferably positioned at the proximal end of the cord, but may also be positioned distal to the capsule.

According to a preferred embodiment, the gastroesophageal diagnostic device is utilized in the following manner. The radioactive isotope in the capsule 222 is first counted in a scintillation counter to quantify the level of radioactivity in the capsule before use. The patient then retains the distal end of the cord 224 near the attachment member 226 and ingests the capsule 222. The capsule 222 is preferably positioned in the lower one-third of the esophagus, approximately five centimeters distal to the lower esophageal sphincter (LES).

The position of the capsule 222 can be determined in several ways. First, if the cord 224 is calibrated with a non-toxic dye, the approximate position of the capsule 222 may be determined by making an estimate based on the length of cord 224 which has been ingested. The location of the capsule 222 can be more precisely determined with the aid of a special camera used to detect gamma radiation. Gamma rays, emitted from the capsule 222, can be detected with a gamma or positron emission tomography (PET) camera. Alternatively, a radiopaque marker on the capsule can be detected with x-rays, or fluoroscopic positioning can be used.

Once the capsule 222 is located at the appropriate position, the attachment member 226 is positioned and fixed in place. For example, if the attachment member 226 is a cap that fits over a tooth of the patient, the clinician may cement the cap over the tooth to hold the cap in place while the patient is undergoing the diagnostic procedure. The attachment member 226 is preferably detachable from the cord or adjustable on the cord to allow the attachment member 226 to be positioned easily. The length of cord 224 necessary to properly position the capsule 222 depends on the size and shape of the patient. Once the proper positioning of the capsule 222 is determined, the adjustable attachment member 226 may be positioned for anchoring the device 200 in place.

At this point, the patient is free to engage in his normal daily activities. Preferably, the gastroesophageal diagnostic device 200 remains in place in the patient for approximately twenty-four hours. Allowing the patient to go through an entire twenty-four hour cycle, including eating, sleeping and other daily activities, provides a more accurate determination of the amount of time that the esophagus is exposed to low pH. Since the device is small, comfortable, and easy to use, there is little to no interference with the patient's normal routine.

After twenty-four hours, the device 200 is removed from the patient. The attachment member 226 is disassociated from the point of attachment, and the cord 224 is used to pull the capsule 222 up from the patient's esophagus. Then the capsule is counted in a scintillation counter to determine the level of radioactivity remaining in the capsule.

The amount of radioactivity in the capsule after the diagnostic procedure is subtracted from the amount of radioactivity which was present in the capsule before the diagnostic procedure. This difference, or the decrease in the amount of radioactivity in the capsule, is used to determine the duration of time, over the twenty-four hour diagnostic period, that the esophagus is exposed to low pH conditions caused by reflux of stomach acid into the esophagus.

To determine the total time of exposure of the esophagus to low pH, the decrease in radioactivity in the capsule is compared to a series of standards. The standards are generated by exposing capsules 222 to samples with the chemical characteristics of gastric acid, including a pH less than pH 4. A standard curve is generated by counting the level of radioactivity remaining in a series of capsules after various times of exposure to pH levels less than pH 4. The radioactive decay that takes place in the capsule over a twenty-four hour period with no exposure to low pH is also taken into account when generating a standard curve. Standards may be generated using either the decrease in the radioactivity in the capsule or the amount of radioactivity retained in the capsule after exposure. If the amount of radioactivity retained in the capsule is used, the initial amount of radioactivity in the capsule should be standardized. By comparing either the decrease in radioactivity in the capsule or radioactivity remaining in the capsule to the corresponding set of standards, a determination can be made of the duration of time that the capsule was exposed to pH levels less than pH 4 and clinically significant for gastroesophageal reflux disease. This information is then used in making a diagnosis regarding gastroesophageal reflux disease.

While the invention has been described and illustrated with reference to specific illustrative embodiments thereof, it is not intended that the invention be limited to those illustrative embodiments. Those skilled in the art will recognize that variations and modifications can be made without departing from the spirit of the invention. It is therefore intended to include within the invention all such variations and modifications that fall within the scope of the appended claims and equivalents thereof.

I claim:

1. A device for determining the duration of exposure of a patient's esophagus to pH levels clinically significant for gastroesophageal reflux disease comprising:
    a capsule containing a known amount of radioactive material, and being subject to pH-dependent degradation at pH less than about pH 4, and being of a size to be readily swallowable;
    a cord, the cord having a proximal end and a distal end, the proximal end being connected to the capsule, whereby the cord allows positioning and retrieval of the capsule.

2. A device according to claim 1 further comprising an attachment member, the attachment member being connected to the distal end of the cord, whereby the attachment member allows the distal end of the cord to be fixed in a selected position.

3. A device according to claim 1 further comprising a weight, the weight being positioned on the cord and adjacent to the capsule.

4. A device according to claim 1 wherein the cord includes measuring indicia along the length of the cord, whereby the measuring indicia allow measurement of the length of cord inserted into a patient.

5. A device according to claim 1 wherein the capsule further comprises a polymer.

6. A device according to claim 1 wherein the amount of radioactive material present in the capsule is about 3 micro-Curies to about 4 micro-Curies.

7. A device according to claim 1 wherein the amount of radioactive material present in the capsule is less than about 3 micro-Curies.

8. A device according to claim 1 wherein the amount of radioactive material present in the capsule is greater than about 4 micro-Curies.

9. A device according to claim 1 wherein the radioactive material is selected from the group consisting of Gallium-67, Molybdenum-99, Indium-111, and Thallium-201.

10. A device according to claim 9 wherein the amount of radioactive material present in the capsule is about 3 micro-Curies to about 4 micro-Curies.

11. A method of detecting gastroesophageal reflux comprising:

provising a gastroesophageal diagnostic device, said gastroesophageal diagnostic device comprising a capsule having a cord attached thereto, the capsule containing a known first level of radioactivity and being subject to pH-dependent degradation at pH levels less than about pH 4;

introducing the gastroesophageal diagnostic device into the esophagus of a patient;

positioning the gastroesophageal diagnostic device in the esophagus of the patient such that the capsule is positioned in the lower one-third of the esophagus;

leaving the gastroesophageal diagnostic device in the esophagus of the patient for a selected time, whereby the capsule degrades and looses radioactivity in a pH-dependent manner;

removing the gastroesophageal diagnostic device from the patient after the selected time;

determining a second level of radioactivity remaining in the capsule after the selected time, calculating the reduction in the amount of radioactivity from the first level of radioactivity in the capsule to the second level of radioactivity in the capsule; and determining the percentage of the selected time during which the capsule was exposed to pH levels less than about pH 4, wherein the reduction in the amount of radioactivity is correlated to the percentage of the selected time during which the capsule was exposed to pH levels less than about pH 4, and wherein exposure of the capsule to pH levels less than about pH 4 for at least a determined percent of the selected time is indicative of gastroesophageal reflux disease.

12. The method of claim 11 wherein the determined percent of the selected time is at least about five percent.

13. The method of claim 11 wherein the determined percent of the selected time is at least about ten percent.

14. The method of claim 11 wherein the determined percent of the selected time is at least about fifteen percent.

15. The method of claim 11 wherein the determined percent of the selected time is greater than about fifteen percent.

16. The method of claim 11 wherein the selected time for leaving the gastroesophageal diagnostic device in the esophagus of the patient is about 24 hours.

17. The method of claim 11 wherein the selected time for leaving the gastroesophageal diagnostic device in the esophagus of the patient is less than 24 hours.

18. A method of determining the duration of exposure of a patient's gastrointestinal tract to pH levels less than about pH 4 comprising:

providing a gastrointestinal diagnostic device, said gastrointestinal diagnostic device comprising a capsule having a cord attached thereto, the capsule containing a known first level of radioactivity and being subject to pH-dependent degradation at pH levels less than about pH 4;

introducing the gastrointestinal diagnostic device into the gastrointestinal tract of a patient;

positioning the gastrointestinal tract of a patient device in the gastrointestinal tract of the patient such that the capsule is positioned at a predetermined location in gastrointestinal tract of the patient;

leaving the gastrointestinal diagnostic device in the gastrointestinal tract of the patient for a selected time, whereby the capsule degrades and looses radioactivity in a pH-dependent manner;

removing the gastrointestinal diagnostic device from the patient after the selected time;

determining a second level of radioactivity remaining in the capsule after the selected time;

calculating the reduction in the amount of radioactivity from the first level of radioactivity in the capsule to the second level of radioactivity in the capsule; and determining the percentage of the selected time during which the capsule was exposed to pH levels less than about pH 4, wherein the reduction in the amount of radioactivity is correlated to the percentage of the selected time during which the capsule was exposed to pH levels less than about pH 4.

* * * * *

UNITED STATES PATENT AND TRADEMARK OFFICE
CERTIFICATE OF CORRECTION

PATENT NO. : 6,475,145 B1
DATED : November 5, 2002
INVENTOR(S) : Richard A. Baylor It is certified that error appears in the above-identified patent and that said Letters Patent is hereby corrected as shown below:

Column 10,
Line 25, delete "tract of a patient device" and substitute -- diagnostic device -- in its place.

Signed and Sealed this

Twelfth Day of August, 2003

JAMES E. ROGAN
*Director of the United States Patent and Trademark Office*